US005177290A

United States Patent [19]

Ryu et al.

[11] Patent Number: 5,177,290

[45] Date of Patent: Jan. 5, 1993

[54] ISOPRENE PROCESS

[75] Inventors: Ji-Yong Ryu, Ramsey; Robert C. Michaelson, Kinnelon, both of N.J.

[73] Assignee: Exxon Chemical Patents Inc., Linden, N.J.

[21] Appl. No.: 639,621

[22] Filed: Jan. 10, 1991

[51] Int. Cl.[5] .......... C07C 1/20; C07C 1/24

[52] U.S. Cl. .......... 585/607; 585/606

[58] Field of Search .......... 585/606, 607, 609, 610

[56] References Cited

U.S. PATENT DOCUMENTS

| | | | |
|---|---|---|---|
| 3,437,711 | 4/1969 | Yanagita et al. | 585/608 |
| 3,502,740 | 3/1970 | Zajacek et al. | 585/609 X |
| 3,574,780 | 4/1971 | Watanabe et al. | 585/606 X |
| 3,621,079 | 11/1971 | Leeds . | |
| 3,714,285 | 1/1973 | Mueller et al. | 585/609 |
| 3,890,404 | 6/1975 | Takagi et al. | 585/607 |
| 3,960,973 | 6/1976 | Stapp | 585/608 X |
| 4,381,416 | 4/1983 | Kyo et al. | 585/606 |
| 4,547,614 | 10/1985 | Vavere | 585/606 |
| 4,593,145 | 6/1986 | Ninagawa et al. | 585/607 |
| 4,734,538 | 3/1988 | O'Connor et al. | 585/606 |

FOREIGN PATENT DOCUMENTS

| | | | |
|---|---|---|---|
| 0272662 | 6/1988 | European Pat. Off. | 585/606 |
| 45-39681 | 12/1970 | Japan . | |
| 57-130928 | 8/1982 | Japan . | |
| 60-042338 | 3/1985 | Japan . | |
| 415906 | 7/1986 | U.S.S.R. . | |
| 415910 | 7/1986 | U.S.S.R. . | |
| 452189 | 7/1986 | U.S.S.R. . | |

OTHER PUBLICATIONS

Albanesi, G. & Mogi, P., Chem. Ind. (Milan), vol. 63, pp. 572–574 (1981).

*Primary Examiner*—W. J. Shine
*Assistant Examiner*—Douglas J. McGinty
*Attorney, Agent, or Firm*—E. F. Sherer; L. K. Russell

[57] ABSTRACT

The present invention is directed to a process for producing dienes which involves reacting a reaction mixture of tertiary alkyl ether and a source of oxygen over two functionally distinct catalysts under reaction conditions sufficient to produce high yields of the dienes with minimal recycle of the ether. The two functionally different catalysts are selected from a group of bifunctional catalysts having both oxidation sites and acidic sites and monofunctional acidic catalysts, such as bifunctional catalysts containing components selected from a group of oxides of vanadium, tungsten, molybdenum, copper, iron, chromium, and uranium and mixtures thereof; and monofuctional acid catalysts such as acid treated montmorillonite clays, and acid catalysts comprising an inorganic amorphous or substantially amorphous oxide material comprising the following components reacted therein:

$M^1/M^2/P/O$ wherein $M^1$ is at least one Group IIIB element selected from the group consisting of Al, Ga, In and Tl; $M^2$ is at least one Group IVb element selected from the group of Si, Sn and Ge. The bifunctional catalysts are used in a first stage reaction, and the monofunctional acidic catalysts are used in a second stage reaction.

32 Claims, 1 Drawing Sheet

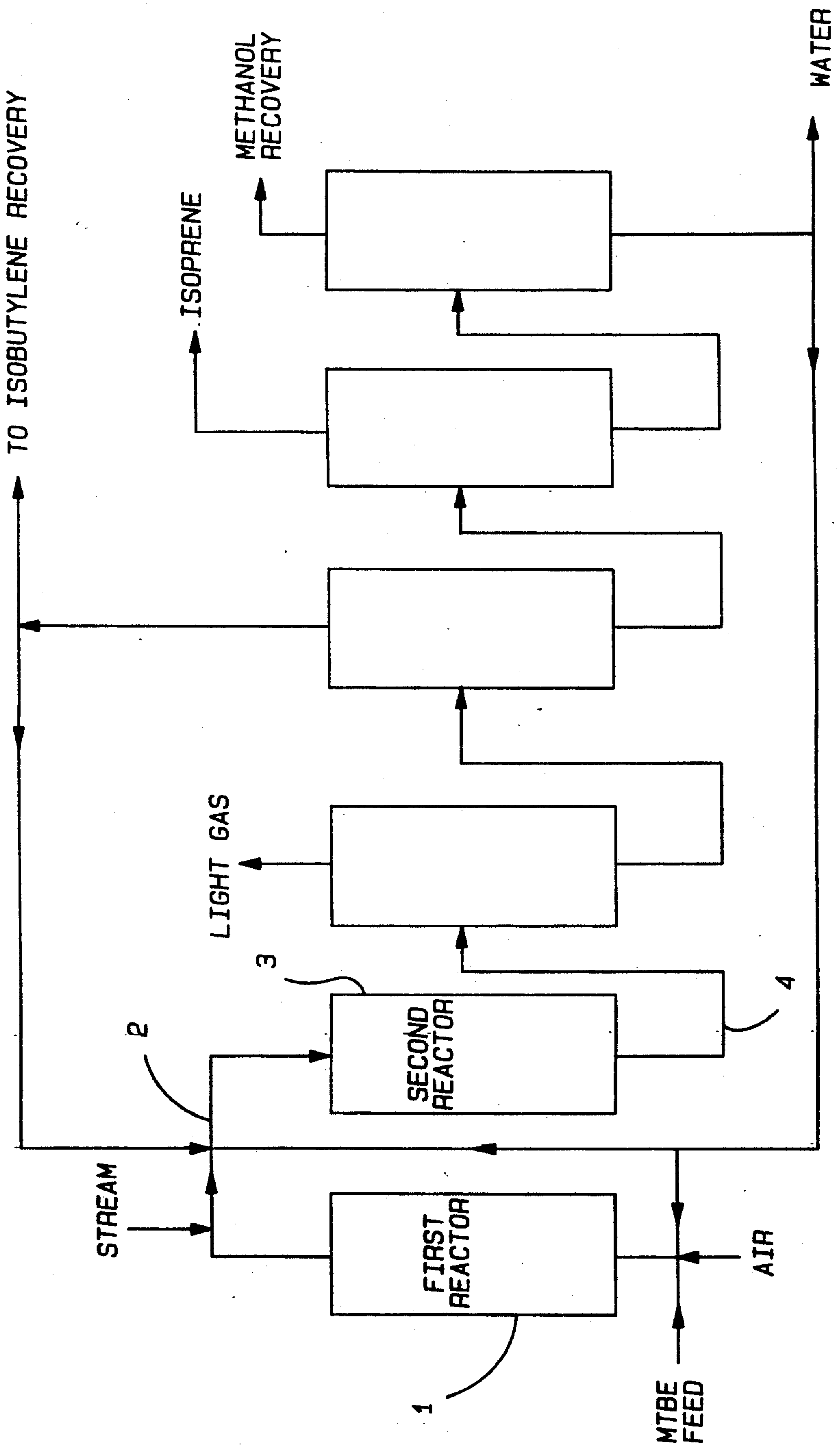
TO ISOBUTYLENE RECOVERY
ISOPRENE
METHANOL RECOVERY
WATER
LIGHT GAS
SECOND REACTOR
FIRST REACTOR
STREAM
AIR
MTBE FEED
1
2
3
4

ISOPRENE PROCESS

BACKGROUND OF THE INVENTION

1. Field of the Invention

The present invention relates to a process for producing conjugated dienes, such as isoprene, from tertiary alkyl ethers, such as MTBE (methyl-tert-butyl ether), and an oxygen source, such as air, over two functionally distinct catalysts.

2. Discussion of Background and Material Information

An isoprene synthesis process is disclosed in U.S. Pat. No. 4,593,145, KURARAY CO., wherein isoprene is produced by passing MTBE and formaldehyde through dilute aqueous acid solution in a stirred tank reactor under pressure. Substances which can release water and formaldehyde may be added between each catalytic stream. Although the conversion of formaldehyde is very high, the conversion of MTBE is moderate, and delicate control of reactor operation is required.

U.S. Pat. No. 3,574,780, SUMITOMO CHEMICAL CO., discloses another process for the manufacture of isoprene. In this process, isoprene is produced by passing the mixture of MTBE and air over mixed oxide catalysts. The feed MTBE is cracked to isobutylene and methanol over the catalyst. The product methanol is oxidized to formaldehyde which reacts with isobutylene over the same catalyst to produce isoprene. The catalyst preparation technique is described in Example 6. The acidic bismuth nitrate solution and the basic mixed solution of ammonium tungstate and molybdate are quickly mixed to form a precipitate at pH 5. This precipitate is kneaded with a silica sol. The mixture is dried and then calcined at 500° C. The calcined mixture is crushed to 12-16 mesh granules.

JP 70-39,681, SUMITOMO, is directed to the production of isoprene from MTBE and oxygen using a catalyst of oxides of molybdenum, vanadium, tungsten or uranium, all of which are known oxidation catalysts, in a one-stage process.

U.S. Pat. No. 3,621,079, SUMITOMO CHEMICAL CO., is also directed to a process for the production of isoprene which involves passing a mixed gas comprising isobutylene, methanol, and dimethyl ether, steam and air over a mixed oxide catalyst.

Commercially, formaldehyde is produced via vapor phase, air oxidation of methanol over iron oxide-molybdenum oxide or silver catalyst. When methanol is oxidized over iron oxide-molybdenum oxide catalyst at 300° C.-400° C. and at atmospheric pressure, the overall yield of formaldehyde which has been produced is as high as 88%-91% carbon oxides, DME and formic acid being typical by-products.

ALBANESI, G. and MOGGI, P., Chem. Ind. (Milan), Vol. 63, P. 572-4 (1981) disclose that the acidic oxides such as alumina, silica-alumina and molecular sieves tend to decompose formaldehyde to CO and $H_2$.

Several Russian publications teach the oxidation of MTBE and methanol to isoprene in a one-stage process. The catalysts can be supported on a silica gel, but acidity of the catalysts are not discussed in the abstracts.

BOLSHAKOV DA, YABLONSKAY AI, CHAPLIN DN, SU-452,189 (i. 86.07.30 f.72.06.15 72SU-797,692) is directed to the production of isoprene by catalytic oxidation of tert butyl methyl ether or mixtures of methanol and isobutylene; this document disclose a method which involves catalytic oxidation of tert-butyl methyl ether or mixtures of methanol and isobutylene at increased temperatures and in presence of catalyst based on W, Mo or Bi oxides which also contain a mixture of rare earth element oxides, i.e., didymium a waste from uranium production. It is disclosed that tests show that the addition of didymium in oxidation of tert-butyl-methyl ether eliminates the need for its preparation from methanol and isobutylene, and increases the yield of isoprene, using recirculation of reaction products, e.g., isobutylene and methanol, to 66%. In the case of oxidation of the mixture of methanol and isobutylene, the reaction is conducted in the gaseous phase, at 280° C. and at a molar ratio of oxygen and isobutylene of 0.32, in presence of catalyst containing oxides of Si, W and didymium, increasing the yield of isoprene to 18.0 wt. % based on starting material isobutylene. The disclosed advantages are increased yield and elimination of by-products, especially formaldehyde.

YABLONSKAY AI, BOLSHAKOV DA, MOROZOVA LA, SU-415,910 (i.86.07.30 f.72.06.15 72SU-797,694) is directed to a catalyst for isoprene production from tert-butyl-methyl ether; the catalyst is described as containing tungsten oxide, didymium and silica gel. To improve efficiency, silica gel is impregnated in aqueous $(NH_4)_2WO_4$ solution, the mixture is dried, and calcined in air. The didymium consists of a mixture of La, Nd, Pr and Sm oxides. A disclosed advantage is improved activity and selectivity of catalyst. In an example, 14.85 g silica gel is impregnated in an aqueous solution containing 21 g $(NH_4)_2WO_4$ and 50 ml $H_2O$, the water is evaporated, the residue is dried at 100° C., impregnated with solution containing 0.15 g didymium in 50 ml 10% HCl, evaporated, dried and calcined for 6 hours at 500° C. in air. The yield of isoprene, using the obtained catalyst, was 12.8 mol. %.

YABLONSKAY AI, BOLSHAKOV DA, MOROZOVA LA, SU-415,906 (i.86.07.30 f.72.06.15 72SU-797,690) is directed to a catalyst for isoprene production which contains molybdenum, bismuth, vanadium, and additionally didymium. It is disclosed that the activity and selectivity of the catalyst, used for production of isoprene by oxidation of tert-butyl methyl ether, were increased by the addition of 0.1-15 wt. % didymium to the mixture of W, Mo, Bi and V oxides. The didymium consists of (in wt. %): 45 La oxide, 38 $Nd_2O_3$, 11 $Pr_6O_{11}$, 4 $Sm_2O_8$ and 2 residues. A disclosed advantage is that the selectivity of the proposed catalyst is 100%, and the yield of isoprene is increased to 65 mol. %. In an example, 14.85 g silica gel is impregnated with solution containing 21 g $(NH_4)_2WO_4$ and 50 ml $H_2O$, excess of water is evaporated and the solid is then treated with solution containing 0.05 g didymium in 50 ml 20% HCl. Solvent is evaporated and the catalyst is dried at 120° C. and calcined for 6 hours at 500° C. in an air stream.

JP 60-042-338, NIPPON-ZEON, relates to the reaction of MTBE and methanol to make isoprene using homogeneous catalysts. The catalysts are acidic and contain transition metals, but there is no indication of an oxidation process. An isobutylene source, such as MTBE, and formaldehyde are reacted with an acid catalyst containing a group IB or IIB metal ion to produce isoprene. JP 60-042,338, NIPPON ZEON, also discloses that certain trivalent metals (Cr, Mo, W, Sb) may be added to reaction mixtures as corrosion inhibitors. While these metals can catalyze oxidation, there is no indication that oxidation is involved. Also, this is a one-stage process.

JP 57-130-928, NIPPON ZEON KK, the preparation of isoprene which involves reacting at least one isobutylene source selected from isobutylene, tert butanol and alkyl tert butyl ether with a formaldehyde source in the presence of water in a liquid phase using an acid catalyst. At least one species of metal ion selected from the elements belonging to Groups Ia, Ib, IIa and IIb is present. A disclosed advantage includes the suppression of by-production of geraniolene while heightening the selectivity of isoprene. In an example, a stainless steel autoclave was charged with 4 wt. pts. of 25% aqueous solution of formaldehyde, 10 wt. pts. of water, 14 wt. pts. of tert butanol, 1 wt. pt. of 85% phosphoric acid, and 0.2 wt. pt. of disodium hydrogenphosphate, followed by charging 7 wt. pts. of isobutylene. The autoclave was immersed in an oil bath heated at 160° C., and was started shaking, and the reaction was allowed to proceed for 25 minutes. The autoclave was then cooled, after which carbon tetrachloride was added. The organic layer was subjected to extraction and subjected to analysis by means of gas-chromatography. The yield of isoprene was 79.5 mol. % relative to formaldehyde and the by-production of geraniolene was only in the yield of 0.8 mol. % relative to formaldehyde.

SUMMARY OF THE INVENTION

The present invention relates to a process for producing isoprene, or other conjugated dienes, from a tertiary alkyl ether such as MTBE (methyl-tert-butyl ether) or TAME (tert amyl methyl ether) and an oxygen source, such as air, over two functionally distinct catalysts. Alternatively, isoolefin and methanol and/or formaldehyde may be used in place of the tert-alkyl methyl ether.

For purposes of the present invention, the functionally distinct catalysts may be arranged in a first stage and a second stage, e.g. in series by being "stacked" in one reactor or contained in two reactors in series.

Although not wishing to be bound by any particular theory, it is believed that the ether is decomposed to the isoolefin and alcohol, e.g., methanol, in the catalyst bed of the first stage, and that the methanol produced is also oxidized to formaldehyde in this first stage bed. The catalyst bed of the second stage causes the formaldehyde to react with the isoolefin to give a "Prins" type intermediate which is subsequently dehydrated to the conjugated diene product, i.e., isoprene in the case of MTBE feed, and 2,3-dimethyl-1,3-butadiene in the case of a TAME feed.

For example, in accordance with the present invention, isoprene is prepared from methyl-tert-butyl ether (MTBE), air and water by reacting them all together first over a bifunctional acid and oxidation catalyst, and then over a functionally different acidic catalyst. The first bifunctional catalyst decomposes MTBE to isobutylene and methanol, and oxidizes the methanol to formaldehyde; the second monofunctional acidic catalyst catalyzes the reaction of formaldehyde with isobutylene to form isoprene. Steam and recycled isobutylene may be added to the stream between the two catalysts.

The present invention, therefore, is directed to a process for producing dienes which involves reacting a reaction mixture comprising a tertiary alkyl ether and a source of oxygen over two functionally distinct catalysts under reaction conditions sufficient to produce high yields of said dienes with minimal recycle of tertiary alkyl ether and tertiary alkyl ether decomposition products, wherein the two functionally distinct catalysts are sequentially arranged, preferably in series comprising a first stage and a second stage.

The present invention is also directed a process for producing conjugated dienes which involves exposing a reaction product comprising isoolefin, alcohol and/or formaldehyde to a monofunctional acid catalyst under reaction conditions effective to yield an intermediate capable of being dehydrated to produce a high yield of a conjugated diene product which is essentially devoid of cyclopentadiene impurity with minimal recycle of isoolefin and formaldehyde. The intermediate is a Prins type intermediate which is preferably selected from the group consisting of a 1,3-diol, and a 1,3-dioxin derived from the 1,3 diol and formaldehyde. In this embodiment, the process preferably also involves reacting a reaction mixture comprising a tertiary alkyl ether and an oxygen source over a bifunctional catalyst to produce said reaction product.

In another embodiment, an isoolefin, or isoolefin precursor, e.g., tertiary alcohol, and alcohol, and/or an aldehyde may be reacted with a source of oxygen over the two functionally distinct catalysts in a manner otherwise similar to the invention as described herein.

For purposes of the present invention the two functionally different catalysts are selected from the group consisting of bifunctional catalysts having both oxidation sites and acidic sites and monofunctional acidic catalysts, wherein the bifunctional catalysts are selected from the group of catalysts consisting of a catalyst containing component as a member selected from the group consisting of oxides of vanadium, tungsten, molybdenum, copper, iron, chromium, and uranium and mixtures thereof, and the monofunctional acid catalysts are selected from the group of acid treated montmorillonite clays, and acid catalysts comprising an inorganic amorphous or substantially amorphous oxide material comprising the following components reacted therein:

$$M^1/M^2P/O$$

wherein $M^1$ is at least one Group IIIB element selected from the group consisting of Al, Ga, In and Tl; $M^2$ is at least one Group VIB element selected from the group of Si, Sn and Ge.

In another embodiment, the present invention is directed to a process for producing conjugated dienes which involves exposing a reaction product comprising a member selected from the group consisting of an isoolefin, an isoolefin precursor, an alcohol, and formaldehyde to a monofunctional acid catalyst under reaction conditions effective to yield an Prins type intermediate capable of being dehydrated to produce a high yield of a conjugated diene product which is essentially devoid of cyclopentadiene impurity with minimal recycle of issoolefin and formaldehyde, which preferably also involves reacting a reaction mixture comprising an tertiary alkyl ether and an oxygen source over a bifunctional catalyst to produce the reaction product which is exposed to the monofunctional catalyst.

In accordance with the present invention, the bifunctional catalysts are used in the first stage, and the monofunctional acidic catalysts are used in the second stage.

For purposes of the present invention, the reaction mixture preferably comprises a member selected from the group consisting of an tertiary alkyl ether, an isoolefin precursor, and mixtures of at least two members selected from the group consisting of a tertiary alkyl ether, an isoolefin precursor, and an alcohol. The diene produced is a conjugated diene.

In the embodiment where the feedstock is tertiary alkyl ether, the tertiary alkyl ether is selected from the group of tertiary alkyl methyl ethers consisting of tert-hexyl-methyl ether, tert-heptyl-methyl ether, tert-amyl methyl ether (TAME) and methyl-tert-butyl ether (MTBE) and the like, and preferably is selected from the group consisting of methyl-tert-butyl ether and tert-amyl methyl ether.

In the embodiment where the tertiary alkyl ether is methyl-tert-butyl ether, the conjugated diene produced is isoprene, and in the embodiment where the isoolefin alkyl ether is tert-aryl methyl ether, the conjugated diene produced is 2,3-dimethyl-1,3-butadiene. In the embodiment where the member is a mixture of an isoolefin and a member selected from the group consisting of alcohols and aldehyde compounds, the alcohol is preferably methanol. In the embodiment where the member is an aldehyde compound, the aldehyde compound may be selected from the group consisting of formaldehyde, formaldehyde dimethyl acetal and formaldehyde methylacetal, the preferred aldehyde compound is formaldehyde.

For purposes of the present invention, reaction conditions comprise a temperature within the range of about 200° C. to about 350° C., a pressure ranging from about atmospheric to several atmospheres, and space velocities within the range of about 0.1 $hr.^{-1}$ to about 10 $hr.^{-1}$, preferably wherein said temperatures are in the range of about 270° C., and the space velocities are within the range of about 0.1 $hr^{-1}$ to about 10 $hr^{-1}$, and preferably within the range of about 0.5 $hr.^{-1}$ to about 2.0 $hr.^{-1}$.

The process of the present invention in producing high yields of conjugated dienes reflected by a conversion of at least about 50% isoolefin to conjugated diene, and preferably a conversion of about 50% to about 90% isoolefin to conjugated diene.

BRIEF DESCRIPTION OF THE DRAWING

The FIGURE is a flow diagram of a process for producing isoprene in accordance with the present invention.

DETAILED DESCRIPTION

In accordance with the present invention, a conjugated diene, such as, isoprene is prepared from an isoolefin, e.g., a tertiary alkyl ether, such as methyl-tert-butyl ether (MTBE), air and water by reacting them all together first over a bifunctional acid and oxidation catalyst, and then over a monofunctional acidic catalyst For example, the first catalyst cracks MTBE to isobutylene and methanol, and oxidizes the methanol to formaldehyde; the second catalyst catalyzes the reaction of formaldehyde with isobutylene to form isoprene.

In contrast to the present invention, a two step route for the synthesis of isoprene from isobutylene and formaldehyde is commercially practiced.

1. Liquid Phase Reaction

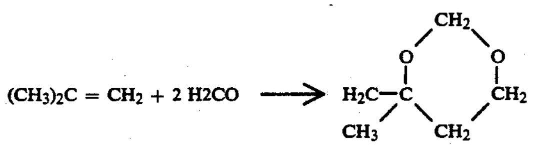

-continued 4,4-Dimethyl-m-dioxane

2. Gas Phase Reaction

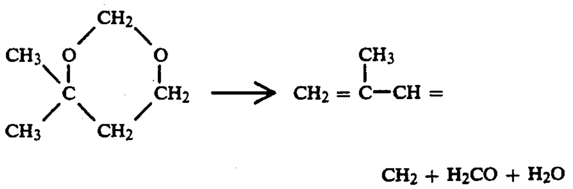

The first step, i.e., the Prins reaction, is performed at 60°-100° C. in the presence of acid catalysts, such as dilute sulfuric acid, under 20 atm. The reaction product, dimethyldioxane, is separated from the reaction mixture by vacuum distillation and then cracked over a solid catalyst to isoprene at an elevated temperature, e.g., 200° C.-400° C.

The disadvantages of such a conventional process are as follows:

i) separation of reaction intermediates are required;

ii) recycle of formaldehyde is necessary because a mole of formaldehyde by-product is produced for every mole of isoprene produced. There are technical problems associated with the formaldehyde separation and recycle; and iii) corrosion resulting from the aqueous acid in the first step.

The bifunctional catalysts used in the first step of the process for producing isoprene in accordance with the present invention are similar to those disclosed in U.S. Pat. Nos. 3,574,780 and 3,621,072 assigned to Sumitomo. These are further described in Examples 1, 2, 3, and 4 below.

The monofunctional, acidic catalysts suitable for purposes of the present invention, which are used in the second step or stage of the reaction process, are of two types: the first being acid treated montmorillonite type clays, e.g. as disclosed in U.S. Pat. No. 4,691,073, MICHAELSON; and the second type being acidic catalysts of the type disclosed in U.S. Pat. No. 4,560,790, RYU. Example 5, described below, relates to a novel method of preparing these catalysts, similar to that disclosed in U.S. Pat. No. 4,560,790, RYU, for a different process.

Almost any isoolefin or tertiary alkyl ether can be used for this reaction depending on the desired product, e.g., using TAME (tert-amyl methyl ether) instead of MTBE would yield 2,3-dimethyl-1,3-butadiene instead of isoprene.

Although the preferred feed is a tertiary alkyl ether, an isoolefin or an isoolefin precursor, e.g., a tert-alcohol and an alcohol, such as methanol, can be used. The substitution of methanol with formaldehyde, or formaldehyde acetal or hemiacetal acetal, is also possible, e.g., as in a recycle operation. Dilution with steam to prevent polymerization of the reactive dienes is also believed to be beneficial; and steam and recycled isobutylene may be added to the stream between the two catalysts.

The reactions in accordance with the present invention operate at quite high temperatures in the range of 270° C., i.e., from 200° C. to 350° C. The pressure range should be from atmospheric to several atmospheres. Space velocities used for purposes of the present invention are in the range of 0.1 to 10 $hr^{-1}$ with 0.5 to 2.0 $hr^{-1}$ being preferred.

In accordance with the present invention, a conjugated diene, i.e., isoprene, is preferably produced by introducing a mixture of a tertiary alkyl ether, such as methyl-tert-butyl ether, air and steam into a series of two reactors which contain the two functionally different catalysts in which case no separation of reaction products from the first reactor is needed prior entering the second reactor.

As previously mentioned, for purposes of the present invention, the first catalyst (catalyst A) is bifunctional and hence it has both oxidation and acidic sites and the second (catalyst B) has only acidic sites. According to the present invention, the catalyst I will be loaded in the first reactor or the first stage of the reactor, and catalyst II in the second reactor or the second stage of the reactor.

The present invention is based on the discovery that when two functionally different catalysts are employed in the previously described manner, a high yield of conjugated diene product, i.e., isoprene, is obtained and the conversion of formaldehyde is sufficiently high that recycle of formaldehyde is unnecessary; moreover, it has been discovered that the conjugated diene, i.e., isoprene, contains no cyclopentadiene impurity.

Referring to the FIGURE, a process in accordance with the present invention is described. A mixture of MTBE and air (and water) is passed through a first reactor loaded with a bifunctional catalyst 1 in which MTBE is cracked to isobutylene and methanol over the acidic sites, and the methanol product is oxidized by air over the oxidation sites to formaldehyde with some of formaldehyde reacting with isobutylene over the acidic sites to produce isoprene.

Steam and recycle isobutylene are then added to reactor effluent stream 2 from the first reactor and then the mixture gas is introduced into a second reactor 3 loaded with a monofunctional acidic catalyst so that there is little or no oxidation of methanol, formaldehyde or isobutylene by air at the reaction temperature employed; in the second reactor, however, there is decomposition of formaldehyde to CO and $H_2$ over the catalysts. The on-line gas chromatographic analysis of the effluent 4 from this second reactor reveals that isoprene yield is very high and the formaldehyde concentration is so low that the recycle of unreacted formaldehyde has no or little merit.

Reactions in the First Reactor

The following examples are concerned with two major reactions which occur in the first reactor: i) the MTBE decomposition to methanol and isobutylene, and ii) methanol oxidation to formaldehyde and methylal, notwithstanding some isoprene is produced over the catalysts.

In the first stage of the process for the producing, the bifunctional catalysts are loaded in a 0.5" i.d.×12" stainless steel reactor which is immersed in a salt bath. Preheated feed enters the bottom of the reactor. The reactor effluent from the top of the reactor is analyzed with an on-line gas chromatograph (GC).

The bifunctional catalysts used in the first stage of the reaction of the present invention are similar to those disclosed in U.S. Pat. Nos. 3,574,780 and 3,621,072, the disclosures of which in their entireties are incorporated by reference thereto herein. In brief, the catalysts suitable for this first step are those which contain, as at least one component, a compound comprising oxygen and one or more members selected from the group consisting of tungsten, vanadium, molybdenum, and uranium (such catalysts will be referred to as "catalysts A," hereinafter). Examples of the catalyst (A) include tungsten (IV, VI) oxide, vanadium (II, III, IV, V) oxide, molybdenum (IV, VI) oxide, uranium (IV, VI) oxide and the like.

Starting materials for preparing catalyst (A) are those shown above or substances capable of being converted into the catalysts (A) by thermal decomposition, such as for example, ammonium heptamolybdate, molybdic acid, ammonium metavanadate, ammonium tungstate, uranyl nitrate, and uranyl acetate.

In addition to these main components, promoters may be added in order to inhibit side reactions and to increase selectivity. For example, compounds of phosphorus, sulfur, boron, antimony, bismuth, tellurium, silver, barium, calcium, magnesium, potassium and sodium are effective for said purpose. (Catalysts incorporated with these promoters will be referred to as "catalysts B", hereinafter). The proportions of the above-mentioned elements in the catalysts can be optionally selected, though said proportions are not irrelevant to conversion and selectivity.

These catalysts A and B may be used after shaping by compression, calcination and the like procedures, without using any carriers or in a state supported on carriers. As the carriers, molten or semi-molten titanium oxide, zinc oxide, tellurium oxide, alumina and active carbon pumice are ordinarily used. Especially preferred as a carrier are compounds of silicon and oxygen (C), such as silica gel. Among the above-mentioned catalysts (A), there are some which display marked isoprene forming ability only when used in combination with the compound (C). Such synergistic effect is observed not only in the case where the catalysts (A,B) are supported on the compound of silicon and oxygen, but also in the case where the catalysts (A,B) and the compound (C) are individually finely-divided and mixed together, and the mixture is compressed for use as a catalyst; and also in the case where a catalyst is prepared by gelling the catalysts (A,B) together with a silica gel in the form of a colloidal dispersion, followed by calcination.

There is a maximum value in isoprene yield depending on the mixing ratio of (A,B) to (C) in the catalyst employed, and the properties and kinds of the starting materials (A,B) and (C), can be selected from the range of 1:99 to 99:1. Generally, a range of from 5:95 to 95:5 gives favorable results.

When silica gel is to be used as a starting material, the use of silica gel having a surface area of less than 350 $m^2$/gm. can greatly increase the isoprene selectivity. The surface area of silica gel employed as a starting material has an important influence on isoprene selectivity, and use of a silica gel small in surface area is preferred.

The promoters employed in the preparation of Catalyst B may be phosphorus compounds. In such case, the catalysts may be prepared, for example, either by mixing phosphomolybdic acid, vanadium phosphate or phosphotungstic acid with silica gel, or by mixing molybdenum trioxide and a suitable amount of phosphoric acid with silica gel. By addition of phosphorus, or a compound of phosphorus and oxygen, the isoprene selectivity based on isobutylene and the amount of isoprene produced per unit volume time of catalyst are increased, and the deposition of carbon on the catalyst surface is inhibited.

Sulfur, or sulfur compounds, also display substantially the same effect as that of phosphorus. In addition thereto, boron or a compound comprising boron and phosphorus, e.g., boron phosphate, shows substantially the same effect. In addition to such substances, as phosphorus, sulfur and boron, which give acidic properties, there may be used, as promoters, such substances which conversely give basic properties, e.g., compounds of alkali or alkaline earth metals, such as sodium, potassium, calcium, barium and magnesium. These substances, when added in small amounts, have actions to increase the isoprene selectivity. Further, tellurium, antimony or bismuth, when incorporated in a small amount, display an action to make catalyst activity extremely mild, and hence can be used as an activity-controlling agent.

For purposes of the present invention, reaction conditions comprise a temperature within the range of about 200° C. to about 350° C., a pressure ranging from about atmospheric to several atmospheres, and space velocities within the range of about 0.1 hr. −1 to about 10 hr. −1, preferably wherein said temperatures are in the range of about 270° C., and the space velocities are within the range of about 0.5 hr. − 1 to about 2.0 hr. − 1.

EXAMPLE 1

A catalyst was prepared by employing a technique similar to that disclosed in U.S. Pat. No. 3,574,780. In so doing, a solution "A" was prepared by dissolving 62.0 g tungstic acid and 14.7 g $(NH_4)_6Mo_7O_{24}\cdot 4H_2O$ in a mixture of 100 cc ammonium nitrate (30%) and 500 cc water. A solution "B" was prepared by dissolving 121 g $Bi(NO_3)_3\cdot 5H_2O$ in a mixture of 50 cc concentrated $HNO_3$ and 600 cc water. The solution "A" was added quickly to the solution "B" with stirring to form a precipitate. After 5 minutes stirring, the pH of the solution was adjusted to 5 by slowly adding concentrated $NH_4OH$ solution. The precipitate was separated again by the filtration. The washed precipitate was mixed with silicic acid paste prepared by mixing 92 g $SiO_3\times H_2O$ (12% weight loss on ignition) with 612 g water. The mixed paste was dried in a vacuum oven at 97° C.–105° C. and then calcined at 500° C. for 18 hours in air. The calcined material was ground to 6–12 mesh granules. The test result of 15cc (6.9 g) catalyst is listed in Table 1.

EXAMPLE 2

A solution "A" was prepared by dissolving 63.6 g $(NH_4)_6Mo_7O_{24}4H_2O$ and 5 g $NH_4VO_3$ in a mixture of 60 cc concentrated $NH_4OH$ and 650 cc water. This is not a true solution (turbid milky $VOSO_4XH_2O$ suspension). A solution "B" was prepared by dissolving 52.5 g $Bi(NO_3)_35H_2O$, 8.3 g $Fe(NO_3)_39H_2O$ and 0.8 g $VOSO_4XH_2O$ (17.98% $H_2O$) in a mixture of 51 cc concentrated $HNO_3$ and 560 cc water. By adding dilute $HNO_3$, the pH of this solution was adjusted to 0.93. The solution "A" was added slowly to solution "B" at room temperature with mechanical stirring over a period of 1 hour and 28 minutes to obtain a precipitate. At the end of the addition, the pH of the mixture was 1.22. By adding concentrated $NH_4OH$ slowly to the mixture over a period of 1 hour and 42 minutes, the pH was adjusted to 5. The precipitate was separated from the mixture by filtration and was thereafter washed with 1600 cc water in the same manner described in Example 1. The washed precipitate was mixed with a silicic acid paste prepared by mixing 82.6 g silicic acid (16% weight loss on ignition ) with 403.8 g water. To this mixture, 58 g acid HF treated montmorillonite powder (−16 mesh), prepared in accordance with a procedure disclosed in U.S. Pat. No. 4,691,073, the disclosure of which in its entirety is incorporated herein by reference thereto, was added and then the mixture was kneaded thoroughly. The mixture was dried at 110° C.–145° C. in a vacuum oven and then calcined at 500° C. in air for 7 hours. The calcined material was ground to 6–12 mesh granules. The test result of 15 cc (6.04 g) is listed in Table 1.

EXAMPLE 3

The following catalyst was prepared for comparison with the catalyst produced following a procedure similar to that of U.S. Pat. No. 3,621,072, which discloses the use of boron as a promoter to improve the selectivity of isoprene.

A solution "A" is prepared by dissolving 14.7 g $(NH_4)_6Mo_7O_{24}4H_2O$ and 0.95 g boric acid in a mixture of 100 cc concentrated $NH_4OH$ and 500 cc water. This is a clear solution. The solution "B" is prepared by dissolving 121 g $Bi(NO_3)_35H_2O$ in a mixture of 50 cc concentrated $HNO_3$ and 600 cc water. By adding concentrated $HNO_3$ slowly, the pH of this solution was adjusted to 0.96. The solution "A" was added slowly to the solution "B" with mechanical stirring over a period of 2 hours 15 minutes to form a precipitate. By adding concentrated $NH_4OH$ solution slowly, the pH of the mixture was adjusted to 5 over a period of 1.5 hours. The precipitate was separated by the filtration. The filter cake was washed with 1500 cc water in the same manner described in Example 1. The washed precipitate was mixed with 80 g silica gel powder (70 u and 300 $m^2/g$ surface area). The mixture was dried at 105°–145° C. and then calcined at 500° C. for 4 hours in air. The calcined material was ground to 6–12 mesh granules. The test result of 15 cc (6.02 g) catalyst is listed in Table 1, above.

TABLE 1

| EXAMPLE NO | MTBE CONV (%) | $CH_3OH$ CONV (%) | ISOPRENE YIELD (%) | $H_2CO$ YIELD (%) | METHYLAL YIELD (%) | DME YIELD (%) | $CO + CO_2$ YIELD (%) | $HCO_2CH_3$ YIELD (%) | MECHO YIELD (%) |
|---|---|---|---|---|---|---|---|---|---|
| 1 | 99.7 | 40.0 | 5.8 | 20.5 | 0.7 | 6.2 | 4.0 | 2.4 | 1.4 |
| 2 | 99.6 | 47.6 | 1.5 | 14.3 | 0.1 | 3.4 | 43.2 | 0.8 | 0.2 |
| 3 | 99.9 | 17.7 | 0.5 | 5.1 | 0.2 | 0.2 | 10.3 | 1.4 | 1.4 |

270° C.; 7.85 cc/hr MTBE feed rate; 64.8 cc/min. air flow; and 15 cc catalyst

EXAMPLE 4

A solution "A" was prepared by dissolving 62.5 g tungstic acid and 15.7 g $(NH_4)_6Mo_7O_{24}4H_2O$ in a mixture of 102 cc concentrated and 500 cc water. A solution "B" was prepared by dissolving 105 g $Bi(NO_3)_35H_2O$ and 16.35 g $Fe(NO_3)_39H_2O$ in a mixture of 50 cc concentrated $HNO_3$ and 600 cc water. The solution "A" was added slowly to the solution "B" with mechanical stirring over a period of 40 minutes to form a precipitate. The pH of the mixture solution was 0.82 at the end of the addition. By slowly adding concentrated $NH_4OH$ over a period of 43 minutes, the pH was adjusted to 5. The precipitate was separated by filtration and then washed with 1600 cc water in the same manner described in Example 1. The washed filter cake was kneaded with a silicic acid paste prepared by mixing 92 g silicic acid (16% weight loss on ignition) with 530 g water. The paste was dried at 95° C.-120° C. and calcined at 500° C. in air for 8 hours. The calcined product was ground to 6-12 mesh granules. The test result of 15 cc (8.03 g) catalyst is listed in Table 2.

catalyst in Example 4 contains Fe in addition to Mo, Bi and W. This catalyst has not only higher methanol oxidation, but also has better selectivity (79%) to useful products (isoprene and formaldehyde).

A small amount of methane is always produced over the catalysts and the amount of methane increases with hours on stream. For example, despite the low methanol conversion in Example 3, the methane gas was detected from the reaction mixture. However, there is no indication of methane in the reaction products in Example 5. The catalyst is composed of mixed oxide of Mo, Bi, Nb, and V supported on silica gel.

TABLE 2

| EXAMPLE NO | MTBE CONV (%) | $CH_3OH$ CONV (%) | ISOPRENE YIELD (%) | $H_2CO$ YIELD (%) | METHYLAL YIELD (%) | DME YIELD (%) | $CO + CO_2$ YIELD (%) | $HCO_2CH_3$ YIELD (%) | MECHO YIELD (%) |
|---|---|---|---|---|---|---|---|---|---|
| 4 | 99.7 | 46.0 | 4.5 | 31.8 | 0.2 | 4.0 | 3.4 | 2.0 | 0.3 |
| 5 | 100.0 | 26.1 | 4.8 | 15.9 | 0.6 | 1.0 | 1.7 | 1.7 | 0.7 |

270° C.; 7.85 cc/hr MTBE feed rate; 64.8 cc/min. air flow; and 15 cc catalyst

EXAMPLE 5

A solution "A" was prepared by stirring 1.19 g vanadium (V) tri-n-propoxide oxide with a basic solution prepared by diluting 6.5 cc concentrated $NH_4OH$ and 1 cc ethylamine with 75 cc water. A solution "B" was prepared by dissolving 6.3 g $(NH_4)_6Mo_7O_{24}4H_2O$ in a basic solution prepared by diluting 38 cc concentrated $NH_4OH$ and 33 cc ethylamine in 250 cc water and then adding 11 g $Nb(OC_2H_5)_5$ to this basic ammonium molybdate solution. A solution "C" was prepared by dissolving 51.8 g $Bi(NO_3)_35H_2O$ and 4 g $Nb(OC_2H_5)_5$ in an acidic solution prepared by diluting 22 cc concentrated $HNO_3$ in 300 cc water.

The solution "A" was added quickly to the solution "B". This mixed solution was added slowly to the solution "C" over a period of 1 hour and 25 minutes with stirring and then stirring was continued for 55 minutes. Finally, the pH of the mixture was adjusted to 5 by slowly adding concentrated $NH_4OH$ over a period of 1 hour and 55 minutes. A yellow precipitate was separated by the filtration. The filter cake was washed with 800 cc water. The filter cake was kneaded with a paste prepared by mixing 9.3 g silicic acid and 36 g silica gel powder (70 u and 300 $m^2/g$ surface area) with water. This mixture paste was dried at 105°-158° C. in a vacuum oven and then calcined at 500° C. for 4 hours in air. The test result of 15 cc (5.02 g) catalyst is listed in Table 2, above.

Discussion of Results

The catalyst in Example 1 is less active for the conversion of methanol to isoprene and formaldehyde than the catalyst in Example 4 which is the preferred catalyst in this invention. The selectivity of undesired products (carbon oxides and methylformate) is 15.5%. The major part of formaldehyde produced is not reacted. Unless this unreacted formaldehyde is recycled, the formaldehyde product is wasted. The catalyst in Example 2 had higher methanol oxidation activity, but it produced mostly useless products. The selectivity of carbon oxides is 76%. This high carbon oxides yield appears to be caused by the inclusion of montmorillonite in the catalyst. The catalyst in Example 3 revealed very low methanol oxidation activity and very low yield of isoprene. The selectivity of carbon oxides is high (58.4%) despite the low methanol conversion. This is contradictory to the statement made in U.S. Pat. No. 3,621,072. The

Reaction in Second Reactor

The next examples show that, when the reactor effluent from the first reactor was introduced with recycle isobutylene and steam to a second reactor, which has been loaded with functionally different type of the catalyst form the one in the first reactor, there is high conversion of formaldehyde, resulting in high yields of isoprene.

The monofunctional acidic catalyst composition used in this second stage of the process of the present invention may be prepared in accordance with the disclosure of commonly-owned U.S. Pat. No. 4,560,790, the disclosure of which in its entirety is incorporated by reference herein thereto. In brief, the catalyst is prepared by reacting at least one metal ($M^1$) hydrocarboxide (referred to herein as Hydrocarboxide I), at least one metal ($M^2$) hydrocarboxide (referred to herein as Hydrocarboxide II), at least one acidic phosphorus-oxygen containing compound, and water in the presence of at least one liquid organic medium under conditions and in a manner sufficient to form a catalyst precursor composition which is then calcined to form an acidic catalyst composition. The resulting catalyst composition comprises an inorganic amorphous or substantially amorphous oxide material comprising the following components reacted therein:

$$M^1/M^2/P/O$$

wherein $M^1$ is at least one Group IIIB element selected from Al, Ga, In, and Tl, preferably aluminum. $M^2$ is at least one Group 4b element selected from Si, Sn, and Ge, preferably Si. For ease of discussion and description, the aforedescribed Group 3b and 4b elements constituting $M^1$ and $M^2$ are referred to generically as metals, although it is recognized that the term "metal" as applied to Si is an unconventional use of this term.

It is to be understood that the precise structure of the metal-phosphorus oxide catalysts of the present invention has not yet been determined although the components of the catalyst composition are believed to be reacted with each other during the preparative procedure and the resulting catalyst is, therefore, not believed to be a mere mixture of oxides.

Hydrocarboxides I and II are selected to be capable of undergoing hydrolysis of the organic portion thereof in the presence of water, and capable of being solubilized or at least partially solubilized in the organic medium and other components of the reaction mixture.

Suitable Hydrocarboxides I which can be employed as the starting material can be represented by the structural formula $$(M^1)(OR)_3 \quad \text{(II)}$$

wherein $M^1$ is, as described above, preferably Al, and R is a substituted or unsubstituted hydrocarbyl radical independently selected from the group consisting of alkyl, typically alkyl having from about 1 to about 8 carbons, preferably from about 2 to about 6 carbons, and most preferably from about 3 to about 4 carbons, aryl, typically aryl having from 6 to about 14 carbons, preferably from about 6 to about 10 carbons, and most preferably 6 carbons, aralkyl, and alkaryl, typically aralkyl and alkaryl wherein the alkyl and aryl portions thereof are as defined immediately above, respectively; cycloalkyl, typically cycloalkyl having from about 4 to about 12 carbons, preferably from about 5 to about 10 carbons, and most preferably from about 6 to about 8 carbons, all of the above-described hydrocarbyl carbon numbers being exclusive of substituents; said R substituents being selected from ether groups, typically ether groups represented by the structural formulae:

$$—O—R_1, —OR_1—OR_2,$$

wherein $R_1$ and $R_2$ are independently selected from the group consisting of alkyl, typically about $C_1$ to about $C_{10}$ alkyl, preferably about $C_1$ to about $C_5$ alkyl, and most preferably about $C_1$ to about $C_3$ alkyl; and ester groups, typically ester groups represented by the structural formulae:

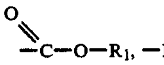, 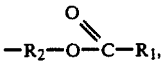, and 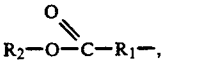, wherein $R_1$ and $R_2$ are as defined above.

Preferred hydrocarboxide I compounds include the alkoxides.

Representative examples of suitable hydrocarboxides I of formula II include: aluminum tri-n-butoxide, sec-butoxide, isobutoxide, isopropoxide, n-propoxide, ethoxide, methoxide, phenoxide, napthoxide, methoxyethoxide, 3-(methoxy carbonyl)propoxide, 3-(ethyl—carbonyl—oxy)butoxide, cyclohexoxide, 1,3,(dimethyl)-2-phenoxide, 1-2(methoxy)-4-phenoxide and mixtures thereof.

Similar representative hydrocarboxides can be formed replacing part, or all of the aluminum present therein with any one or more of the other aforedescribed Group 3b elements.

The preferred hydrocarboxides I include aluminum, tri-sec-butoxide, n-butoxide, n-propoxide, isopropoxide, methoxide, ethoxide; and mixtures thereof.

Hydrocarboxide II which is employed as a starting material in the precursor forming reaction can be represented by the structural formula:

$$(M^2)(OR)_4 \quad \text{(III)}$$

wherein $M^2$ and R are as described above in connection with structural formulae I and II above, respectively. The specific hydrocarboxide R groups can be the same as illustrated above in connection with the aluminum hydrocarboxides and can be employed with any of the aforedescribed Group 4b elements.

Preferred hydrocarboxides II include silicon: tetraethoxide, tetra-n-propoxide, tetraisopropoxide, tetramethoxide, tetra-n-butoxide, tetraisobutoxide, and mixtures thereof.

The acidic phosphorus-oxygen containing compound which can be employed as a starting material must possess at least one acidic hydrogen and be capable of reacting with the hydrocarboxides I and II or the hydrolyzed inorganic product thereof, and the use of the term "acidic phosphorus oxygen compound" is indicative of this requirement. Representative examples of suitable acidic phosphorus-oxygen containing compounds include phosphorus acid, phosphinous acid, phosphenous acid, phosphoric acid, phosphonic acid, phosphine oxide, phosphoranoic acid, a phosphorane dioic acid, phosphorane trioic acid, phosphoranetetroic acid, phosphorane pentoic acid, as well as any of the aforenoted acids having one or more but not all of the acidic hydrogens replaced with an alkyl group, typically $C_1$ to $C_{10}$ preferably $C_1$ to $C_5$ and most preferably $C_1$ to $C_3$ alkyl.

In addition, polyphosphoric acid, an acid commercially available as a mixture of orthophosphoric acid with pryophosphoric, triphosphoric and higher acids, sold on the basis of its calculated $H_3PO_4$ content (e.g., 115%), and super phosphoric acid sold at 105% $H_3PO_4$ content, can also be employed as starting materials.

The preferred acidic phosphorus-oxygen compound is phosphoric acid.

Another group of acidic catalysts used during the second reaction, also referred to is the second stage of the reaction, are those preferably produced in accordance with the disclosure of U.S. Pat. No. 4,691,073, the disclosure of which is hereby incorporated in its entirety by reference herein thereto.

These catalysts preferably are prepared by reacting a naturally occurring or synthetic clay with HF or HCl followed by calcining. The reacting or incorporation of the HF of HCl with the clay can be accomplished by any means such as contacting the clay with anhydrous HF or HCl gas or by impregnation of the clay with the aqueous acid (e.g., mixing method equilibrium adsorption method, evaporation-to-dryness method, spraying method)

Preferably the clay is reacted with 1.0 to 70 wt. %, preferably 20 to 50 wt. % hydrofluoric acid or 1.0 to 37%, preferably 20 to 30 wt. % hydrochloric acid at temperatures of 0° C. to 50° C., preferably 10° C. to 30° C., for 30 to 120 minutes. The amount of the acid is 0.001 to 1.0 preferably 0.01 to 0.10 grams anhydrous acid/gram clay. Following reaction, the fluid is decanted and the clay is then preferably washed first with water and then with alcohol before calcining.

The calcining temperature is selected so as to achieve a highly active high surface area catalyst of a moisture content of less than 5% by wt. Preferably, temperatures are 250° C. to 1000° C., and more preferably 400° C. to 700° C.

The calcination is generally carried out in air, but an atmosphere of an inert gas (e.g., nitrogen, carbon dioxide, argon), steam or mixtures thereof may also be used. The time for calcination is generally 0.1 to 24 hours, preferably 0.5 to 10 hours, although it depends upon the calcination temperature. The amount of the fluorine or chlorine compound supported on the carrier is 0.1 to 100 parts by weight of the carrier, preferably 1.5% to 6.0%.

As examples of the carrier containing silicon oxides used in the present invention, there may be mentioned minerals such as silica, montmorillonite, kaolinite, attapulgite, bentonite and acid clay. Besides these, silica-alumina, silica-zirconia, silica-magnesia and their mixtures may also be used. Silica may be used in either the form of gel or sol. A particularly preferred carrier is one prepared from attapulgite or montmorillonite type minerals. The surface area of the carrier is not particularly limiting, but preferably it is more than 1 $m^2/g$, more preferably above 40 $m^2/gm$. Preferred surface areas after calcination are in the range of 100 $m^2/gm$ to 400 $m^2/gm$.

EXAMPLE 7

Ammonium nitrate (17.4 g) was dissolved in a dilute nitric acid solution, prepared by diluting 21.3 cc concentrated $HNO_3$ and 14.2 cc HF (48-51%) with 500 cc water. To this solution, 49.7 g montmorillonite extrudate used in Example 5 was added and stirred for 1 hour. After decant, the same acid solution treatment was repeated twice. The montmorillonite extrudate was washed twice in a dilute $HNO_3$ solution, prepared by diluting 14.2 cc concentrated $HNO_3$ with 500 cc water and washed with 500 cc water. The washed extrudate was calcined at 250° C. for 1.5 hours, 400° C. for 0.5 hours and then 500° C. for an hour in air. The test result of this catalyst is listed in Table 3.

TABLE 3

| EXP NO | T | FEED COMP (%) TBA | DMM | $H_2O$ | MEOH | FEED RATE (LMSV) | CT* (SEC) | TBA CONV (%) | $H_2CO$ CONV (%) |
|---|---|---|---|---|---|---|---|---|---|
| 7 | 270 | 35.9 | 4.9 | 57.1 | 2.1 | 1.4 | 2.6 | 99.8 | 71.4 |
| 8 | " | " | " | " | " | 0.9 | 3.9 | 99.8 | 55.0 |
| 9 | " | " | " | " | " | 1.4 | 2.6 | 99.9 | 69.1 |
| 10 | " | 82.3 | 12.0 | 5.7 | 0.0 | 0.9 | 2.6 | 99.9 | 66.9 |
| 11 | " | 70.8 | 10.4 | 14.6 | 4.2 | 1.0 | 5.5 | 99.9 | 89.7 |
| 12 | " | " | " | " | " | 1.5 | 3.7 | 99.9 | 86.8 |
| 13 | " | " | " | " | " | 1.0 | 5.5 | 99.9 | 91.8 |
| 14 | " | " | " | " | " | 1.5 | 3.7 | 99.9 | 74.9 |
| 15 | " | " | " | " | " | " | 5.3 | 99.9 | 61.9 |

| EXP NO | ISOPRENE YIELD (%) | $CO + CO_2$ SELEC (%) BASED ON $H_2CO$ | CATALYST |
|---|---|---|---|
| 7 | 64.5 | 9.6 | MONTMORILLONITE |
| 8 | 54.3 | 1.4 | MIXED OXIDE OF P, Al & Si |
| 9 | 65.4 | 5.4 | MONTMORILLONITE |
| 10 | 58.3 | 9.7 | MONTMORILLONITE |
| 11 | 85.2 | 0.9 | MIXED OXIDE OF P, Al, Nb & Si |
| 12 | 82.1 | 2.2 | MONTMORILLONITE |
| 13 | 87.2 | 0.4 | MIXED OXIDE OF P, Al & Si |
| 14 | 54.4 | 27.3 | ALUMINA |
| 15 | 59.8 | 0.8 | MIXED OXIDE OF P, Al & Si |

*CT; contact time

EXAMPLE 6

Ammonium nitrate (60 g) was dissolved in dilute nitric acid solution prepared by diluting 10 cc concentrated $HNO_3$ in 1500 cc. To this solution, 200 g 1/16" montmorillonite extrudate (calcined at 550° C. for 3 hours) was added and stirred for 2 hours. After decant, the montmorillonite extrudate was washed twice with 750 cc water. After drying at 120°-140° C., calcined at 500° C. for 5 hours in air.

In a half-inch stainless steel reactor, 15 cc (5.48 g) of the catalyst described in Example 5 at the bottom on the inlet side and 3 cc (1.79 g) of the previously described montmorillonite catalyst at the top of the reactor on the inlet side were loaded. The reaction was carried out exactly in the same manner as Example 5. The methanol conversion was 32.7%. The yields of isoprene and formaldehyde were 13.1 and 7.9%, respectively. The carbon oxide's yield was 3.6%. By stacking the two functionally different catalysts in a reactor, the yield of isoprene was more than doubled compared with Example 5. The formaldehyde content in the reactor effluent was reduced to about half of those of Example 5. It is also interesting to compare the results of Examples 2 and 6. The catalyst in Example 2 contained the montmorillonite, which showed very poor yield of isoprene and formaldehyde. Carbon oxides were the major product of the methanol oxidation.

EXAMPLE 8

Preparation of the Solution "A"

Tetraethyl orthosilicate (92.4 g) and aluminum sec-butoxide were dissolved in a mixture of diethyl ether (624.7 g), and 267 cc acetone.

Preparation of the Solution "B"

A phosphoric acid solution was prepared by mixing 17.9 g 85% $H_3PO_4$, 18.7 g water, and 134 cc acetone in an ice bath.

Preparation of the Solution "C"

An aluminum sec-butoxide solution was prepared by mixing 15.8 g aluminum sec-butoxide in a mixture of 85 cc ether and 40 cc acetone and kept in an ice bath until its use.

Preparation of the Solution "D"

Another phosphoric acid solution was prepared by mixing 71.6 g 85% $H_3PO_4$, 8.33 g $H_2O$, and 65 cc acetone in an ice bath.

The solution "B" was slowly added to the solution "A" with mechanical stirring at room temperature over a period of 1 hour and 42 minutes, and then stirring was continued for 34 minutes. The solution "C" was added and then stirring was continued for 34 minutes. To this mixture, the solution "D" was added slowly at room temperature over a period of 2 hours, aged at room temperature with stirring for 17 hours, and refluxed for 2 hours. White precipitate was filtered. The filter cake was dried at 114°-120° C. in a vacuum oven for 5 hours and then calcination was carried out at 450° C. for 1 hour and 520° C. for 4.5 hours in air. The calcined filter cake was ground to a powder (minus 16 mesh). The powder (21.82 g) was mixed with 4.58 g aqueous saturated starch solution and the pelletized (0.5" diameter). The pellets were calcined at 460° C. for 4 hours and 650° C. for 7.5 hours in air. The calcined pellets were ground to 6-16 mesh granules. The test result of this catalyst is listed in Table 3.

EXAMPLE 9

Ammonium nitrate (16.6 g) was dissolved in an acidic solution, prepared by diluting 20.3 cc concentrated $HNO_3$ and 13.5 cc (HF 48-51%) with 500 cc water. To this solution, 47.4 g montmorillonite extrudate (see Example 6) was added and stirred for 1 hour. After decantation, the extrudate was washed with dilute nitric acid solution prepared by diluting 13.5 cc concentrated $HNO_3$ with 500 cc water. Repeated the above acid treatment, except that the stirring was continued for 2 hours. The extrudate was washed twice with the dilute acid solution and then with 500 cc water. After drying the montmorillonite, it was calcined at 250° C. for 0.5 hours and then 500° C. for 17 hours. The test result of this catalyst is listed in Table 3.

EXAMPLE 10

The same catalyst in Example 9 was tested for a feed of different compositions. See Table 3, above, for the result.

EXAMPLE 11

Preparation of Solution "A"

Tetraethyl orthosilicate (125.9 g), 37.9 aluminum tri-sec-butoxide and 3 g niobium pentaethoxide were mixed with a mixture of acetone (281 g) and ethyl ether (698.7 g). The solution was stirred for 30 minutes before use.

Preparation of the Solution "B"

Water (17.5 g) and 17.5 g 85% $H_3PO_4$ were mixed with a mixture of acetone (138 g) and ether (16 g) in an ice bath.

Preparation of the Solution "C"

Aluminum sec-butoxide (12 g), 8.1 g niobium pentaethoxide and 6.7 g tetraethyl orthosilicate were mixed with 134.1 g diethyl ether.

Preparation of Solution "D"

Water (19.1 g) and 6 g 85% $H_3PO_4$ were mixed with 138.5 g acetone in an ice bath. The solution "B" was slowly added to "A" solution with mechanical stirring over a period of 2.9 hours. When 75% of the solution "B" had been added, 200 cc ether was added to the mixture and then the addition of the solution "B" was continued. At the completion of the addition of the solution "B", the solution "C" was added to the mixture and then stirred for half an hour. The solution "D" was slowly added over a period of 1.8 hours, aged at room temperature with stirring for 17 hours. The white precipitate in the mixture was filtered. The filter cake was dried in a vacuum oven for 2.5 hours at 60° C. and then 120° C. overnight. The dried cake was calcined at 460° C. for 3.5 hours and then 600° C. overnight in air. The calcined cake was ground to powder (minus 16 mesh). The powder was pelletized to 0.5" diameter pellets. The pellets were calcined at 500° C. overnight and 650° C. for 7.5 hours in air. The calcined pellets were ground to 6-16 mesh granules. See Table 3 for the test result.

EXAMPLE 12

The catalyst in Example 9 was tested again with another feed of different composition. See Table 3 for the result.

EXAMPLE 13

The catalyst in Example 8 was tested with a feed of different composition. See Table 3 for the test result.

EXAMPLE 14

Active, acidic alumina catalyst (190 $m^2/g$) was tested. See Table 3 for the result.

EXAMPLE 15

The catalyst in Example 8 was further calcined at higher temperatures: 750° C. for 16 hours and 830° C. for 3 hours in air. The result is listed in Table 3.

Discussion of Results

The conversion of formaldehyde and isoprene yield are very high compared to those of the examples in U.S. Pat. Nos. 3,574,780, 3,621,079 and 4,593,145. In Examples 11, 12 and 13, the conversions of formaldehyde are sufficiently high, that separation of formaldehyde from the reaction mixture and formaldehyde recycle is not necessary as a practical matter. Even if the recycle of formaldehyde to the second reactor is carried out, these examples demonstrate that the process for producing isoprene in accordance with the present invention is superior to the manufacture of isoprene by these conventional processes.

The catalyst in Example 2, which contains montmorillonite, produced CO and $CO_2$ as major products of methanol oxidation. However, Examples 6, 7, 9, 10 and 12 show that the undesirable side reactions for CO and $CO_2$ are greatly reduced when the montmorillonite is physically separated from the methanol oxidation catalyst.

The processes disclosed by SUMITOMO, discussed earlier, have been observed to result in very low conversion to isoprene and need to recycle large amounts of unreacted isoolefin as well as formaldehyde. These disadvantages are largely avoided by the present invention which uses a bifunctional catalyst, with acidic catalysts, as discussed in Examples 6-15, in either a stacked bed or series reactor configuration. The stacked/series bed configuration, as supported by Example 2, produces large quantities of CO and $CO_2$ when the reactor beds are not separated. Table 3 indicates that excellent yields of isoprene can be obtained when using monofunctional acidic catalysts in series with bifunctional catalysts.

The montmorillonite and other catalysts suitable for purposes of the present invention, e.g., the mixed oxides of Si, Al, and P decompose formaldehyde very little due at least in part to the fact that the calcination temperature of the mixed oxides of Si, Al and P in the present invention are lower, i.e., less than about 650° C., than conventional calcination at temperatures within the range of about 880° C.–930° C. of the prior art metal oxides.

Although the invention as described with reference to particular means, materials and embodiments, from the foregoing description, one skilled in the art can easily ascertain the essential characteristics of the present invention; and various changes and modifications may be made to various usages and conditions, without departing from the spirit and scope of the invention as described in the claims that follow.

What is claimed is:

1. A process for producing dienes, said process comprising:

reacting a reaction mixture comprising tertiary alkyl ether and a source of oxygen over two functionally distinct catalysts, wherein said two functionally different catalysts comprise bifunctional catalysts having both oxidation sites and acidic sites, and monofunctional acidic catalysts selected from the group consisting of acid treated montmorillonite clays, and acid catalysts comprising an inorganic amorphous or substantially amorphous oxide material comprising the following components reacted therein:

$M^1/M^2/P/O$ wherein $M^1$ is at least one group IIIB element selected from the group consisting of Al, Ga, In and Tl; and $M^2$ is at least one group 4b element selected from the group consisting of Si, Sn and Ge, said two functionally different catalysts being separately arranged in a first stage and a second stage wherein said bifunctional catalysts are used in said first stage and said monofunctional acidic catalysts are used in said second stage, under reaction conditions sufficient to produce high yields of said dienes with minimal recycle of said tertiary alkyl ether and tertiary alkyl ether decomposition products.

2. The process for producing dienes of claim 1, wherein said bifunctional catalysts are selected from the group of catalysts comprising a catalyst containing component selected from the group consisting of oxides of vanadium, tungsten, molybdenum, copper, iron, chromium, and uranium, and mixtures thereof.

3. The process for producing dienes of claim 1, wherein said reaction mixture comprises a reactant selected from the group consisting of tertiary alkyl ether, an isoolefin precursor, and mixtures of at least two members of the group consisting of a tertiary alkyl ether, an isoolefin precursor, and an alcohol.

4. The process for producing dienes of claim 3, wherein said diene is a conjugated diene.

5. The process for producing dienes of claim 3, wherein said isoolefin precursor is a tertiary alcohol ether.

6. The process for producing dienes of claim 3, wherein said tertiary alkyl ether is a tertiary alkyl methyl ether selected from the group consisting of tert-heptyl methyl ether, tert-hexyl methyl ether, tert-amyl methyl ether and methyl-tert-butyl ether.

7. The process for producing dienes of claim 6, wherein said tertiary alkyl ether is a member selected from the group consisting of methyl-tert-butyl ether, and tert-amyl methyl ether.

8. The process for producing dienes of claim 7, wherein said tertiary alkyl ether is methyl-tert-butyl ether.

9. The process for producing dienes of claim 8, wherein said conjugated diene is isoprene.

10. The process for producing dienes of claim 9, wherein said isoolefin alkyl ether is tert-amyl methyl ether.

11. The process for producing dienes of claim 10, wherein, said conjugated diene is 2,3-dimethyl-1,3-butadiene.

12. The process for producing dienes of claim 4, wherein said reactant is a mixture of a member selected from the group consisting of an isoolefin and an isoolefin precursor, and a member selected from the group consisting of alcohols and aldehyde compounds.

13. The process for producing dienes of claim 12, wherein said conjugated diene is isoprene.

14. The process for producing dienes of claim 13, wherein said reactant is an alcohol.

15. The process for producing dienes of claim 13, wherein said reactant is an aldehyde compound and is a member selected from the group consisting of formaldehyde, formaldehyde dimethyl acetal, and formaldehyde methyl acetal, and mixtures of formaldehyde, formaldehyde dimethyl acetal, and formaldehyde methyl acetal.

16. The process for producing dienes of claim 15, wherein said aldehyde compound is formaldehyde.

17. The process for producing dienes of claim 4, wherein said reaction conditions comprise a temperature within the range of about 200° C. to about 350° C., a pressure ranging from about atmospheric to several atmospheres, and space velocities within the range of abut 0.1 $hr.^{-1}$ to about 10 $hr.^{-1}$.

18. The process for producing dienes of claim 17, wherein said temperature is about 270° C.

19. The process for producing dienes of claim 17, wherein said space velocities are within the range of about 0.5 $hr.^{-1}$ to about 2.0 $hr.^{-1}$.

20. A process for producing conjugated dienes, said process comprising:

reacting a reaction mixture comprising a tertiary alkyl ether and an oxygen source over a bifunctional catalyst to produce a reaction product comprising a member selected from the group consisting of an isoolefin, an isoolefin precursor, an alcohol, and formaldehyde;

exposing said reaction product to a monofunctional acid catalyst under reaction conditions effective to produce a high yield of a conjugated diene product which is essentially devoid of cyclopentadiene impurity with minimal recycle of isoolefin and formaldehyde.

21. The process for producing conjugated dienes of claim 20, wherein said monofunctional acid catalysts are selected from the group of acid treated montmorillonite clays, and acid catalysts comprising an inorganic amorphous or substantially amorphous oxide material comprising the following components reacted therein:

$M^1/M^2/P/O$ wherein $M^1$ is at least one group IIIB element selected from the group consisting of Al, Ga, In and Tl; $M^2$ is at least one Group IVB element selected from the group of Si, Sn and Ge.

22. The process for producing conjugated dienes of claim 21, wherein said bifunctional catalysts are selected from the group of catalysts consisting of a catalyst containing component selected from the group consisting of oxides of vanadium, tungsten, molybdenum, copper, iron, chromium, and uranium and mixtures thereof.

23. The process for producing conjugated dienes of claim 22, wherein said tertiary alkyl ether is a tertiary alkyl methyl ether.

24. The process for producing conjugated dienes of claim 23, wherein said tertiary alkyl ether is a tertiary alkyl methyl ether selected from the group consisting of tert alkyl methyl ether, tertiary-hexyl methyl ether, tert-amyl methyl ether and methyl-tert-butyl ether.

25. The process for producing conjugated dienes of claim 24, wherein said isoolefin alkyl ether is a member selected from the group consisting of methyl-tert-butyl ether and tert-amyl methyl ether.

26. The process for producing conjugated dienes of claim 25, wherein said isoolefin alkyl ether is methyl-tert-butyl ether.

27. The process for producing conjugated dienes of claim 25, wherein said conjugated diene is isoprene.

28. The process for producing conjugated dienes of claim 25, wherein said isoolefin alkyl ether is tert-amyl methyl ether.

29. The process for producing conjugated dienes of claim 28, wherein said conjugated diene is 2,3-dimethyl-1,3-butadiene.

30. The process for producing conjugated dienes of claim 25, wherein said reaction conditions comprise a temperature within the range of abut 200° C. to about 350° C., a pressure ranging from about atmospheric to several atmospheres, and space velocities within the range of abut 0.1 $hr.^{-1}$ to about 10 $hr.^{-1}$.

31. The process for producing dienes of claim 30, wherein said temperatures are in the a range of about 270° C.

32. The process for producing dienes of claim 31, wherein said space velocities are within the range of about 0.5 $hr.^{-1}$ to about 2.0 $hr.^{-1}$.

* * * * *